United States Patent
Burnett (10) Patent No.: US 10,010,644 B2
(45) Date of Patent: Jul. 3, 2018

(54) PHOTOCATALYTIC DEVICE FOR DUCTLESS HEATING AND AIR CONDITIONING SYSTEMS

(71) Applicant: Dust Free, LP, Royse City, TX (US)

(72) Inventor: Gregg William Burnett, Royse City, TX (US)

( * ) Notice: Subject to any disclaimer, the term of this patent is extended or adjusted under 35 U.S.C. 154(b) by 306 days.

(21) Appl. No.: 14/691,912

(22) Filed: Apr. 21, 2015

(65) Prior Publication Data

US 2015/0224218 A1 Aug. 13, 2015

Related U.S. Application Data

(63) Continuation-in-part of application No. 13/483,896, filed on May 30, 2012, now Pat. No. 9,011,780.

(51) Int. Cl.
  *A61L 9/20* (2006.01)
  *A61L 9/22* (2006.01)
  *B01D 53/88* (2006.01)

(52) U.S. Cl.
  CPC .............. *A61L 9/205* (2013.01); *A61L 9/22* (2013.01); *B01D 53/885* (2013.01); *B01D 2255/802* (2013.01); *Y10T 29/49885* (2015.01)

(58) Field of Classification Search
  CPC ............. A61L 2/205; A61L 9/205; A61L 9/20
  See application file for complete search history.

(56) References Cited

U.S. PATENT DOCUMENTS

| | | |
|---|---|---|
| 2,881,854 A | 4/1959 | Uehre, Jr. |
| 4,859,329 A | 8/1989 | Fink |
| 5,011,609 A | 4/1991 | Fink |
| 5,120,435 A | 6/1992 | Fink |
| 5,236,585 A | 8/1993 | Fink |
| 5,523,057 A * | 6/1996 | Mazzilli ............ A61L 9/20 250/436 |
| 5,578,113 A * | 11/1996 | Glenn ............ B03C 3/155 261/107 |
| 5,919,422 A | 7/1999 | Yamanaka et al. |
| 6,221,314 B1 * | 4/2001 | Bigelow ............ A61L 9/20 250/432 R |
| 6,546,883 B1 | 4/2003 | Fink et al. |

(Continued)

FOREIGN PATENT DOCUMENTS

| | | |
|---|---|---|
| CN | 2392106 Y | 8/2000 |
| CN | 2922905 Y | 7/2007 |

(Continued)

*Primary Examiner* — Donald R Spamer (74) *Attorney, Agent, or Firm* — Fogarty LLP (57) ABSTRACT

A photocatalytic device comprising Manganese dioxide and Titanium dioxide coated housing, an ultraviolet light source disposed therein, and a plurality of multi-metallic photocatalytic structures, such as hydrated multi-metallic catalyst substrates, is adapted to be deployed in conjunction with the exchange air intake of a mini-split system. The photocatalytic device has (a) Manganese dioxide and Titanium dioxide coated reflector(s) that is/are positioned to reflect ultraviolet light onto the photocatalytic structures. The photocatalytic device may have at least one carbon fiber and/or needle type ionizer disposed in the housing. The photocatalytic device may also have at least one sensor and may be wirelessly coupled to a computing device or controller.

25 Claims, 7 Drawing Sheets

(56) References Cited

U.S. PATENT DOCUMENTS

| | | | |
|---|---|---|---|
| 6,730,265 B2 * | 5/2004 | Horton, III | A61L 9/205 250/455.11 |
| 6,752,970 B2 | 6/2004 | Schwartz et al. | |
| 6,784,440 B2 | 8/2004 | Fink et al. | |
| 6,849,107 B1 * | 2/2005 | Huffman | B01D 46/0005 250/436 |
| 6,949,228 B2 | 9/2005 | Ou Yang et al. | |
| 6,997,185 B2 | 2/2006 | Han et al. | |
| 7,160,566 B2 | 1/2007 | Fink et al. | |
| 7,635,659 B2 | 12/2009 | Naganuma et al. | |
| 7,871,518 B2 | 1/2011 | Ellis et al. | |
| 7,988,923 B2 | 8/2011 | Fink et al. | |
| 2001/0046461 A1 * | 11/2001 | Hamilton | A61L 2/10 422/200 |
| 2003/0077211 A1 | 4/2003 | Schwartz et al. | |
| 2003/0150708 A1 | 8/2003 | Fink | |
| 2003/0230477 A1 | 12/2003 | Fink et al. | |
| 2004/0016887 A1 | 1/2004 | Fink et al. | |
| 2004/0056201 A1 | 5/2004 | Fink et al. | |
| 2004/0156959 A1 | 8/2004 | Fink et al. | |
| 2004/0197243 A1 | 10/2004 | Schwartz et al. | |
| 2005/0163653 A1 | 7/2005 | Crawford et al. | |
| 2005/0186124 A1 | 8/2005 | Fink et al. | |
| 2005/0238551 A1 * | 10/2005 | Snyder | A61L 9/205 422/186.3 |
| 2006/0144690 A1 | 7/2006 | Fink et al. | |
| 2006/0163135 A1 * | 7/2006 | Ellis | D06F 35/001 210/251 |
| 2006/0201119 A1 * | 9/2006 | Song | A61L 9/16 55/471 |
| 2006/0228275 A1 | 10/2006 | Rutman et al. | |
| 2006/0266221 A1 | 11/2006 | Fink et al. | |
| 2007/0000407 A1 | 1/2007 | Leong | |
| 2007/0107597 A1 * | 5/2007 | Cheung | B01D 53/885 96/16 |
| 2007/0110860 A1 | 5/2007 | Fink et al. | |
| 2007/0243114 A1 * | 10/2007 | Morrow | C09D 1/00 422/121 |
| 2009/0041617 A1 * | 2/2009 | Lee | A61L 2/208 422/4 |
| 2009/0183943 A1 | 7/2009 | Leistner et al. | |
| 2009/0217690 A1 | 9/2009 | Silderhuis | |
| 2010/0120347 A1 * | 5/2010 | Gehring | B60H 1/345 454/155 |
| 2011/0250125 A1 | 10/2011 | Fink et al. | |

FOREIGN PATENT DOCUMENTS

| | | |
|---|---|---|
| CN | 101245939 A | 8/2008 |
| CN | 201135626 Y | 10/2008 |
| DE | 20211178 U1 | 11/2002 |
| WO | WO 2006/134149 A1 | 12/2006 |

* cited by examiner

PHOTOCATALYTIC DEVICE FOR DUCTLESS HEATING AND AIR CONDITIONING SYSTEMS

RELATED APPLICATIONS

This is a continuation in part of U.S. patent application Ser. No. 13/483,896 also entitled Photocatalytic Device for Ductless Heating and Air Conditioning Systems, filed May 30, 2012, the disclosure of which is hereby incorporated by reference herein in its entirety.

TECHNICAL FIELD

Embodiments of the invention are directed, in general, to oxidation technology for air purification systems and, more specifically, to a photocatalytic device that is adapted to be used with ductless heading and air conditioning systems.

BACKGROUND

Air-source heat pumps transfer heat between a building and the outside air. Heat pumps are popular because of their low cost and capability to do an excellent job of heating, cooling and dehumidifying. For homes without ducts, air-source heat pumps are available in a ductless version called a ductless mini-split heat pump that has two parts—an indoor unit and an outdoor unit. The mini-split products are typically super-efficient, energy star rated, and reliable. Both the indoor and outdoor units are basically silent. A mini-split heat pump provides a cost-effective, environmentally friendly, heating and cooling system.

A typical mini-split system is used to maintain indoor air quality. However, the primary function of most heating and air conditioning systems is to control the temperature and humidity of the air. Many indoor air pollutants, such as volatile organic compounds (VOCs), cannot be removed by typical mini-split systems.

A photocatalytic air purifier is based on photocatalytic oxidation (PCO), a technology that converts fine particles and/or toxic gasses into safer compounds. Generally speaking, a photocatalytic air cleaner may use broad-spectrum, ultraviolet light, which reacts with a chemical catalyst (e.g., thin-film titanium dioxide-based material) to oxidize organic compounds, thus reducing or eliminating certain microorganisms otherwise present in the air.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Often, an air cleaning device may be added to ducts in a heating and air conditioning systems to remove VOCs. Photocatalytic air cleaning devices are a common technique for indoor air purification and deodorization. A photocatalytic air cleaning device in a HVAC system is typically a duct-mounted device that comprises an ultraviolet lamp illuminating a photocatalytic filter to create free radicals that eliminate VOCs. Mini-split systems do not have ducts and, therefore, cannot use existing photocatalytic air cleaning devices.

In one embodiment, a photocatalytic device is adapted to be externally mounted on a mini-split system. The photocatalytic device may be mounted in any location that allows airflow to or from the mini-split to pass through the device. For example, the photocatalytic device may be mounted at an intake or supply vent or at an exhaust or return vent of a mini-split system. Such system and method embodiments may include a housing adapted for deployment in conjunction with an air exchange intake of an indoor unit of a mini-split system, at least a portion of an interior surface of the housing coated with a Manganese dioxide and Titanium dioxide coating.

In embodiments, the photocatalytic device comprises an ultraviolet light source and one or more catalyst substrates that are adapted to support a hydroxyl radical reaction with water vapor that results in hydro peroxides and hydroxyl ions. Such a photocatalytic device may be positioned at the intake of a mini-split system to clean the air space serviced by the heating and cooling system.

In other embodiments, the photocatalytic device may be adapted to be retrofitted to existing or installed mini-split systems.

Various embodiments may include one or more Manganese dioxide and Titanium dioxide coated reflectors located within the housing and positioned adjacent to the first and second catalyst substrates to distribute reflected light from the ultraviolet light source across a surface of the catalyst substrates.

In accordance with embodiments of the present systems and methods, the catalyst substrates may comprise a hydrated multi-metallic catalyst, with the catalyst comprising a plurality of compounds and/or elements selected from Manganese dioxide, Titanium dioxide, Titanium, Zinc, Platinum, Gold, Silver, Copper, Rhodium, Ruthenium, Lanthanum, and/or Fluoride.

In some embodiments at least one ionizer may be disposed in the housing, adapted to provide ions within the housing. Therein the ionizer(s) may be is a needle type ionizer and/or a carbon fiber type ionizer, and may produce either positively charged ions or negatively charged ions.

In accordance with various embodiments of the present systems and methods at least one sensor is coupled to photocatalytic device, the sensor configured to determine a status of the photocatalytic device. A wireless transmitter coupled to the sensor, may be configured to transmit an indication of the status to a controller, a personal computer, and/or a portable computing device. In such embodiments, a wireless receiver in the photocatalytic device may be adapted to receive commands from the controller, a personal computer, and/or a portable computing device to control operation of the ultraviolet light source, or the like.

In various embodiments, one or more of the techniques described herein may be performed by one or more computer systems. In other various embodiments, a tangible computer-readable storage medium may have program instructions stored thereon that, upon execution by one or more computer systems, cause the one or more computer systems to execute one or more operations disclosed herein. In yet other various embodiments, one or more systems may each include at least one processor and memory coupled to the processors, wherein the memory is configured to store program instructions executable by the processor(s) to cause the system(s) to execute one or more operations disclosed herein.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

Having thus described the invention in general terms, reference will now be made to the accompanying drawings, which are not necessarily drawn to scale, and wherein:

DETAILED DESCRIPTION

The invention now will be described more fully hereinafter with reference to the accompanying drawings. This invention may, however, be embodied in many different forms and should not be construed as limited to the embodiments set forth herein. Rather, these embodiments are provided so that this disclosure will be thorough and complete, and will fully convey the scope of the invention to those skilled in the art. One skilled in the art may be able to use the various embodiments of the invention.

Figure 1:
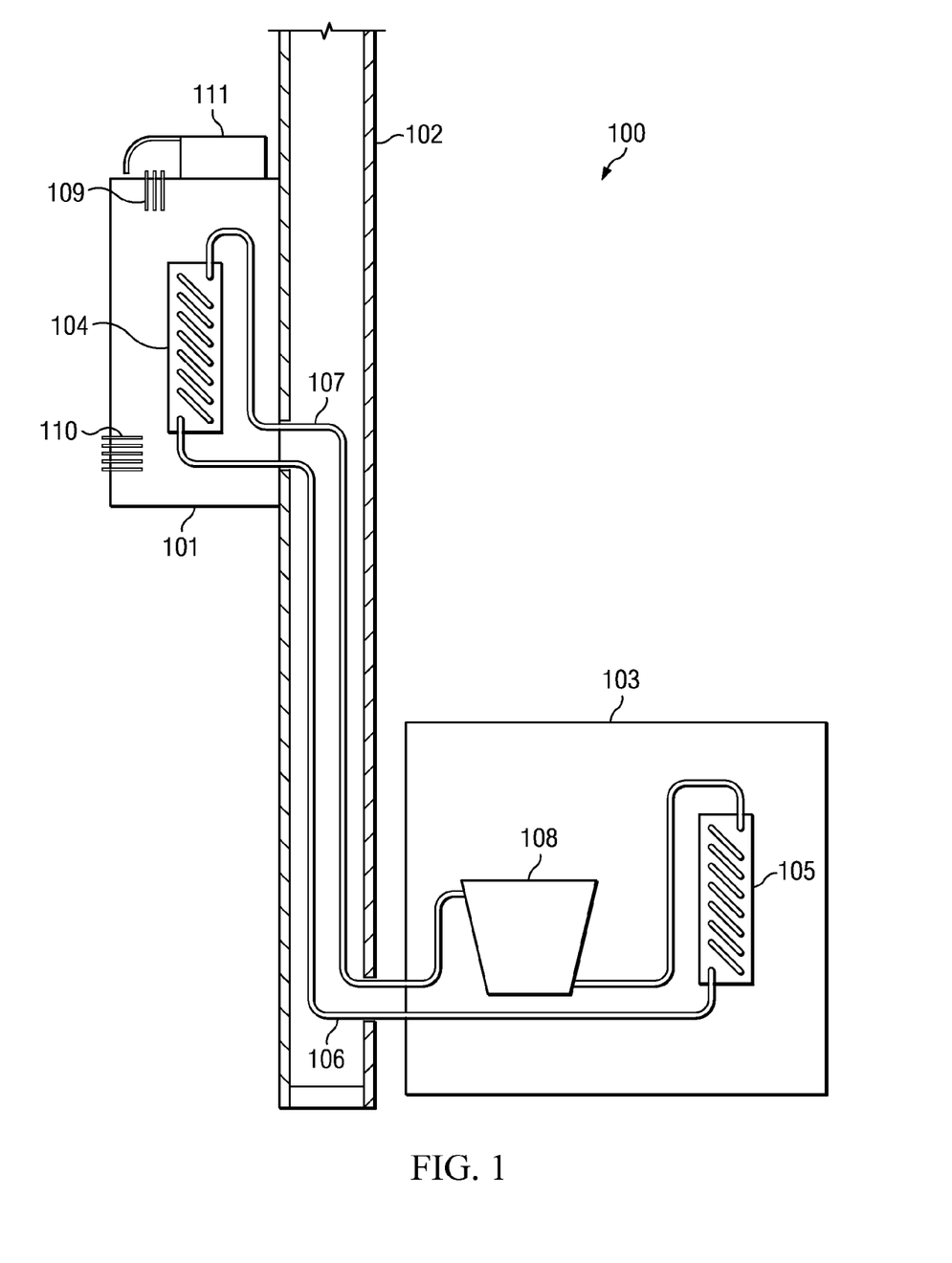
FIG. 1 is a block diagram illustrating a mini-split heating and cooling system.

FIG. 1 is a block diagram illustrating a mini-split heating and cooling system 100, which may offer an energy-efficient alternative to typical furnaces and air conditioners. Indoor unit 101 is mounted inside a building on wall 102. Outdoor unit 103 is mounted outside the building on wall 103. During the cooling season, heat exchanger 104 of indoor unit 101 extracts heat from inside the building and then sends it outside the building to outdoor unit 102. During the heating season, heat exchanger 105 extracts heat from the colder outside air and sends it into the building to indoor unit 101. Tubes 106 and 107 and compressor 108 are used to circulate refrigerant through the system.

Indoor unit 101 has an intake vent 109 that allows airflow to enter the unit and pass by or through heat exchanger 104. Exhaust vent 110 allows heated/cooled air to flow into the room for heating/cooling. In one embodiment, a photocatalytic device 111 is positioned near intake 109. Intake air flow passes through photocatalytic device 111, which may use ultraviolet light to significantly reduce the amount of microbials in the air space. This helps to reduce possible health problems associated with inhaling microbials. The ultraviolet light within photocatalytic device 111 is also beneficial in keeping the coils of heat exchange 104 free of mold, which increases system efficiency.

Ultraviolet (UV) light represents the frequency of light between 185 nanometers (nm) and 400 nm and is invisible to the naked eye. Within the UV spectrum lie three distinct bands of light: UV-A, UV-B, and UV-C. Longwave UV light (315 nm to 400 nm) or UV-A refers to what is commonly called "black light." UV-B (280 nm to 315 nm) or midrange UV is the type of light that causes sunburn. Germicidal UV light (185 nm to 280 nm) or UV-C is effective in microbial control. Research has demonstrated that UV light between 254 nm and 265 nm is most efficient for microbial destruction. Germicidal lamps that produce the majority of their output in this range are the most effective in microbial control and destruction.

Figures 2, 3:
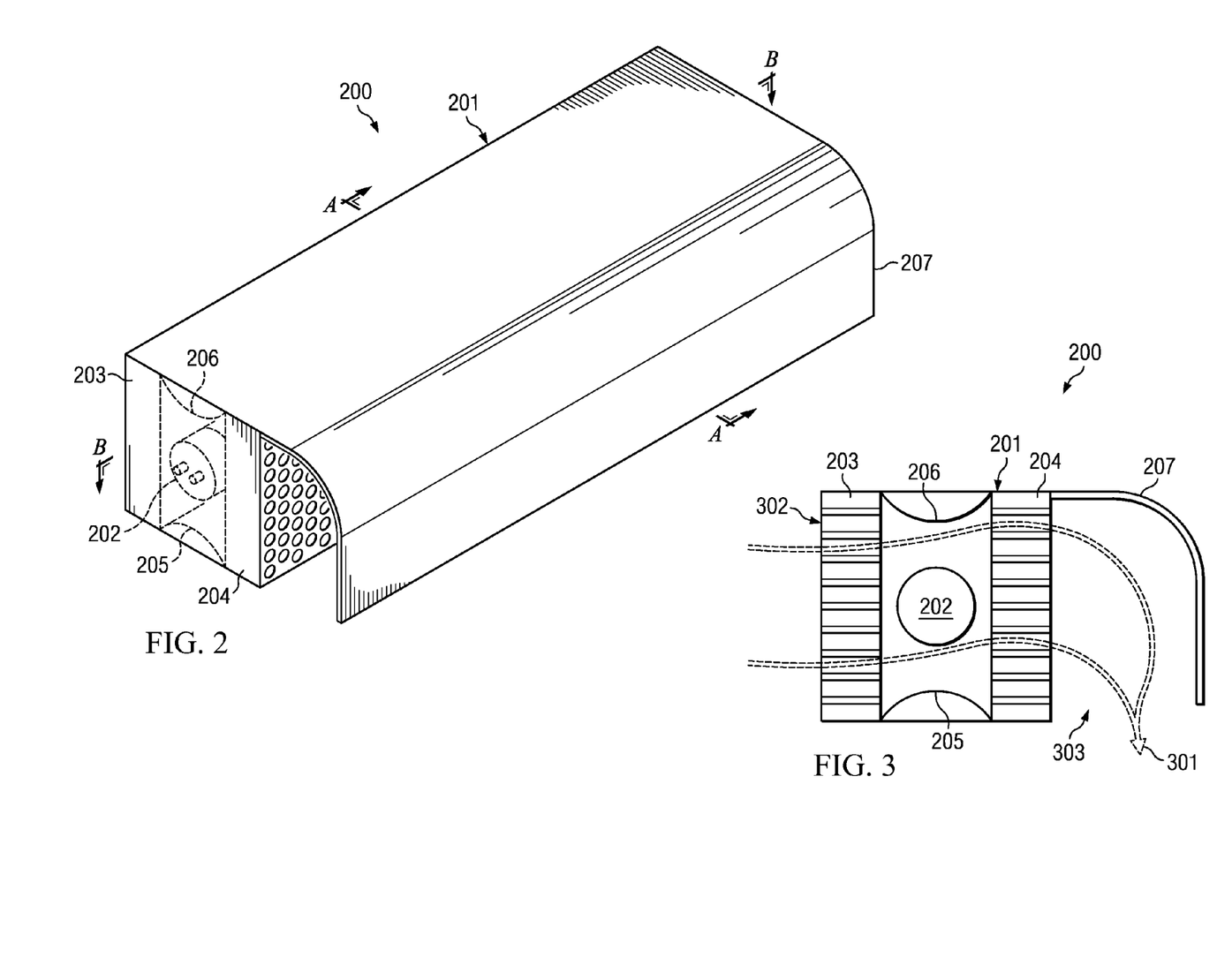
FIG. 2 is a block diagram of a photocatalytic device adapted for use with a mini-split system according to one embodiment.
FIG. 3 is a cross section view of the photocatalytic device according to one embodiment.

FIG. 2 is a block diagram of a photocatalytic device 200 adapted for use with a mini-split system according to one embodiment. Photocatalytic device 200 includes housing 201. An ultraviolet light source 202 is positioned near photocatalytic structures 203 and 204 in housing 201. In one embodiment, the photocatalytic structures 203 and 204 are comprised of a plurality of fluted structures arranged in a honeycomb formation. Ultraviolet light from source 202 illuminates the photocatalytic structures 203 and 204. Curved reflective surfaces 205 and 206 are adapted to reflect ultraviolet light from source 202 so that the ends of photocatalytic structures 203 and 204 receive the ultraviolet light rays at an angle that is as perpendicular as possible.

The photocatalytic structures 203 and 204 may be, for example, a hydrated catalytic matrix. The hydrated catalytic matrix may comprise any catalytic compound, element, or combination thereof. In one embodiment, the hydrated catalytic matrix may be a hydrated multi-metallic catalyst multi-metallic catalytic matrix, such as a hydrated quad-metallic catalyst. When the ultraviolet light 202 impacts the photocatalytic structures 203 and 204, ozone is produced in the catalytic matrix. The catalyst supports a hydroxyl radical reaction with water vapor that results in hydro peroxides, hydroxyl ions, super oxide ions, passive negative ions hydroxides, and ozonide ions. These are highly reactive chemical species. The hydroxyl radicals are very strong oxidizers and will attack organic materials. This creates oxidation that helps to reduce odors, volatile organic compounds (VOCs), airborne viruses, bacteria, mold and other types of air pollution. The catalytic matrix may be comprised of Manganese dioxide, Titanium dioxide, Titanium, Zinc, Platinum, Gold, Silver, Copper, Rhodium, Ruthenium, Lanthanum, and/or Fluoride, for example. In other embodiments, other combinations of rare and noble metals may be used in a multi-metallic catalytic matrix. Additional elements, such as Carbon may also be included in the catalytic matrix.

Additional embodiments of the catalytic matrix may comprise adsorbent materials, such as one or more of Zeolite, Potassium Permanganate, Manganese Dioxide, and Activated Carbon. Adsorbents may be used to capture molecular-sized pollutants, odors, and non-particulates and to remove VOCs.

Ultraviolet light source 202 may be, for example, a high-intensity, broad-spectrum ultraviolet bulb or tube. In other embodiments, the ultraviolet source may be a low pressure fluorescent quartz bulb or a medium pressure amalgam lamp. Ultraviolet light falls in the band of light between 185 nm and 400 nm. There are three distinct bands of light within the ultraviolet spectrum: UV-A, UV-B, and UV-C. Longwave UV light (315 nm to 400 nm), or UV-A, refers to what is commonly called "black light." Midrange UV (280 nm to 315 nm), or UV-B, causes sunburn. Germicidal UV light (185 nm to 280 nm), or UV-C, is effective in microbial control. Research has demonstrated that the most efficient frequency for microbial destruction is between 254 nm and 265 nm within the UV-C band. Germicidal lamps that produce the majority of their output in this range will be the most effective in microbial control/destruction.

The curved reflectors 205 and 206 are positioned to reflect ultraviolet light from ultraviolet light source 202 to the internal face of photocatalytic structures 203 and 204. As a result, photocatalytic structures 203 and 204 receive both direct ultraviolet light from source 202 and reflected ultraviolet light from curved reflectors 205 and 206 as described in pending U.S. patent application Ser. No. 13/353,419, filed Jan. 19, 2012 and entitled "Photocatalytic Device with Curved Reflectors," the disclosure of which is hereby incorporated by reference herein in its entirety. In one embodiment, reflectors 205 and 206 are curved in a manner that optimizes the distribution of ultraviolet light across the faces of photocatalytic structures 203 and 204. In other embodiments, bent reflectors may be preferable to curved reflectors 205 and 206. The size, shape and angle of such bent reflectors would be selected to optimize the uniform distribution of ultraviolet light across the surfaces of target structures 203 and 204. It will be understood that other convex shapes may also be used for the reflectors in other embodiments.

In operation, air flows through photocatalytic structure 203, past ultraviolet light source 202, then through photocatalytic structure 204. As the air exits photocatalytic structure 204, it is directed downward by shield 207 into the intake vent (not shown) of a mini-split system.

FIG. 3 is a cross section view of photocatalytic device 200 along line A-A of FIG. 2. Arrow 301 illustrates how airflow moves through device housing 201. Air enters device housing 201 at face 302 of photocatalytic structure 203, passes thorough photocatalytic structures 203 and 204, and is deflected by shield 207 to exit at opening 303.

Figure 4:
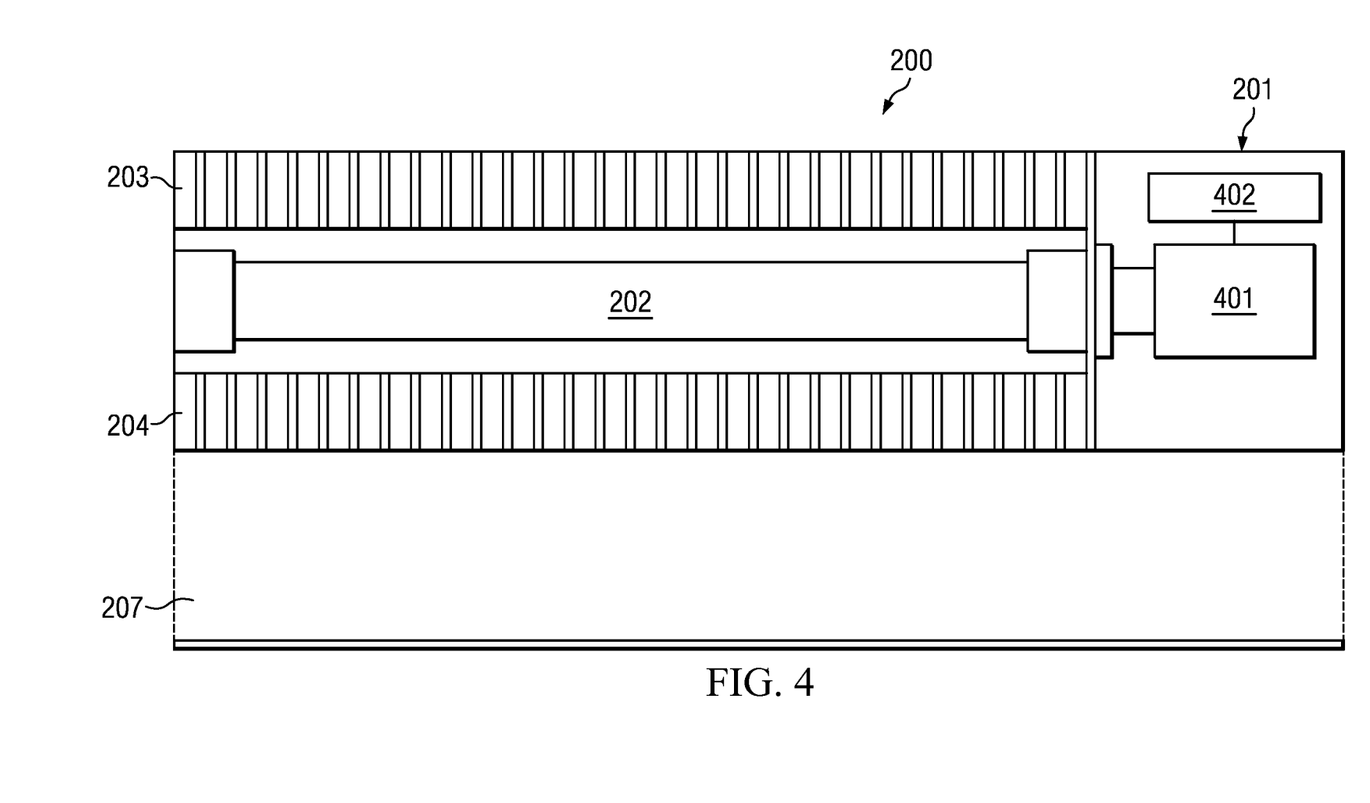
FIG. 4 is another cross section view of the photocatalytic device according to one embodiment.

FIG. 4 is a cross section view of photocatalytic device 200 along line B-B of FIG. 2. Ballast 401 controls the amount of electricity provided to ultraviolet source 202 from power supply 402. Power supply 402 may be a battery, A/C transformer, or any other source of electric current.

Figure 5:
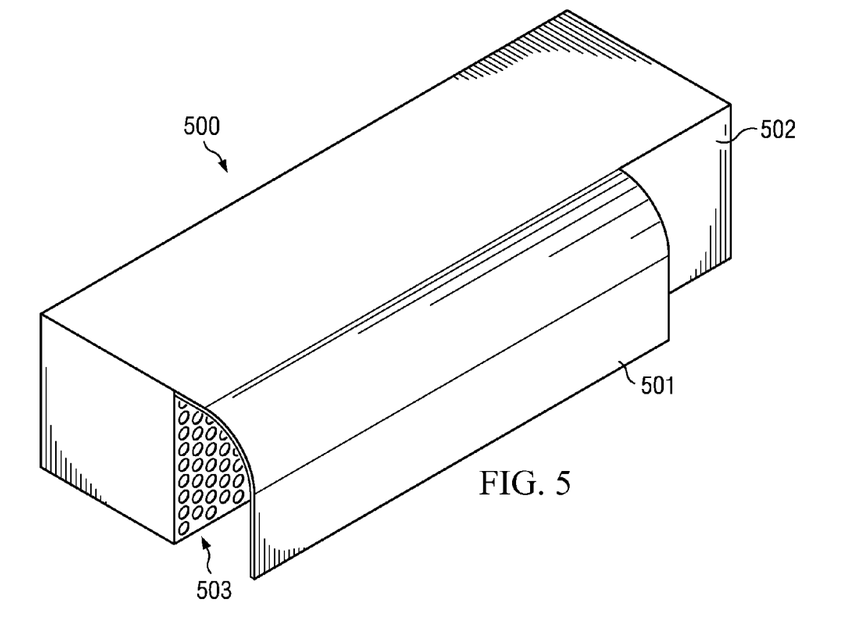
FIG. 5 illustrates an alternate embodiment of the photocatalytic device in which output shield expends partially across the front of the device.

FIG. 5 illustrates an alternate embodiment of the photocatalytic device (500) in which output shield 501 expends partially across the front of the device. Air does not flow through area 502, which may contain a power supply and ballast as shown in FIG. 4. Shield 501 extends the length of photocatalytic structure 503 and is adapted to divert airflow out of the device and into a mini-split system or other input (not shown).

Figure 6:
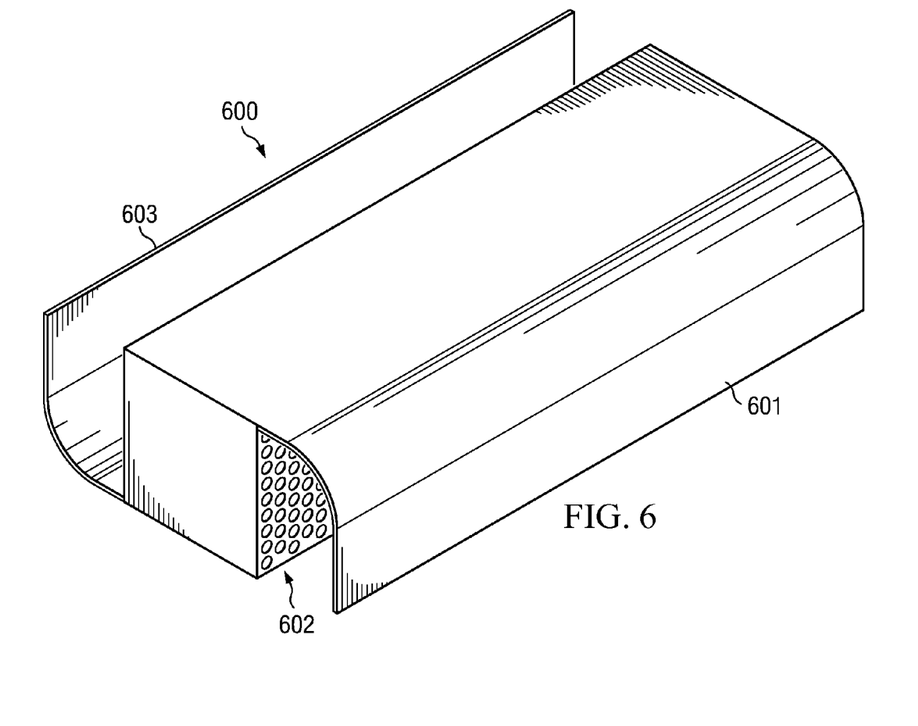
FIG. 6 illustrates a further alternative embodiment of the photocatalytic device.

FIG. 6 illustrates a further alternative embodiment of the photocatalytic device (600). Output shield 601 extends the length of the device and is adapted to divert airflow out of photocatalytic structure 602 into a mini-split system or other input (not shown). Also, input shield 603 extends the length of the device and is adapted to channel airflow into and input photocatalytic structure of device.

Figure 7:
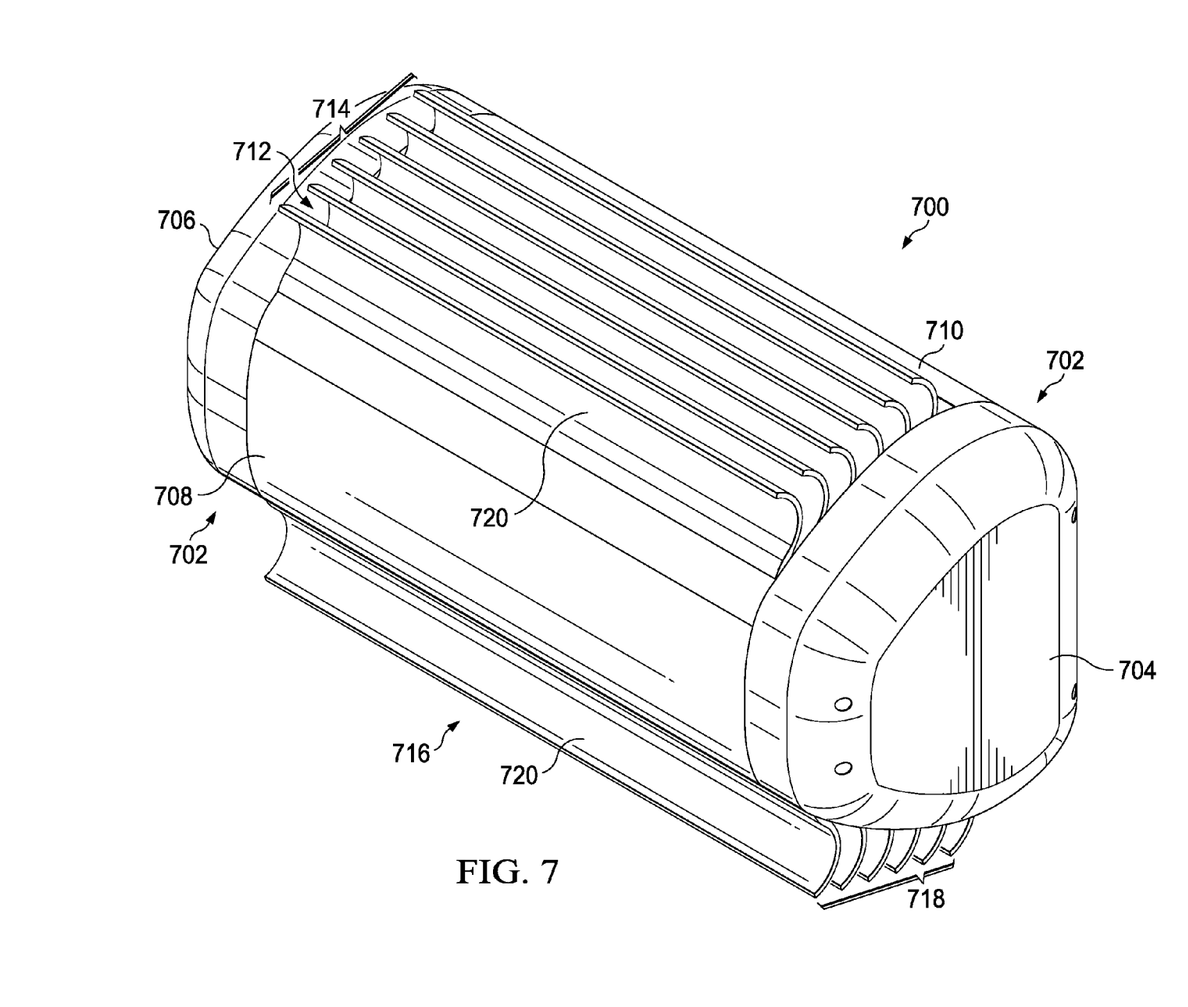
FIG. 7 is a perspective view of another example embodiment of a photocatalytic device adapted for use with a mini-split system.
Figure 8:
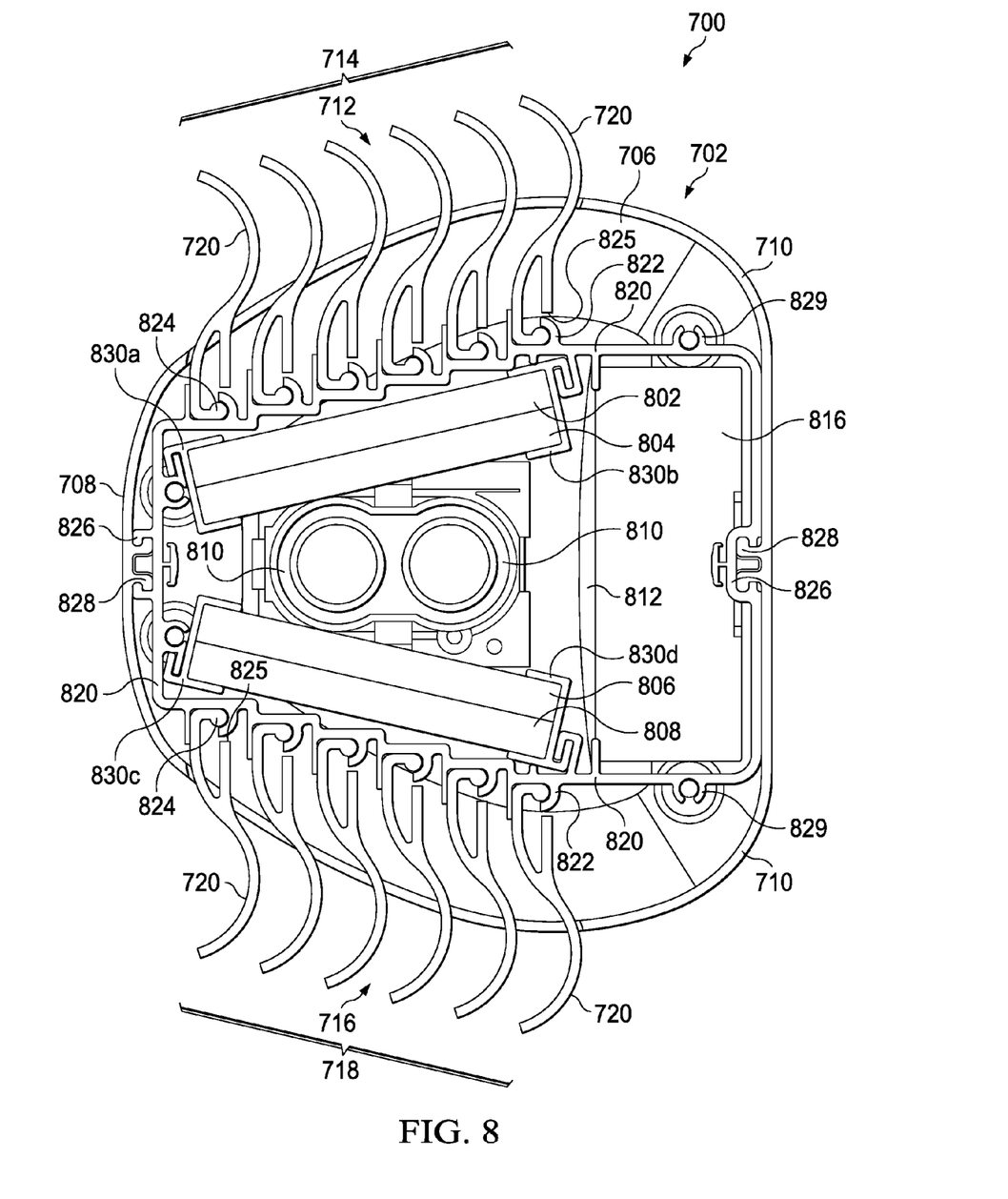
FIG. 8 is a fragmentary, generally cross-sectional, end view of the example embodiment of a photocatalytic device of FIG. 7.
Figure 9:
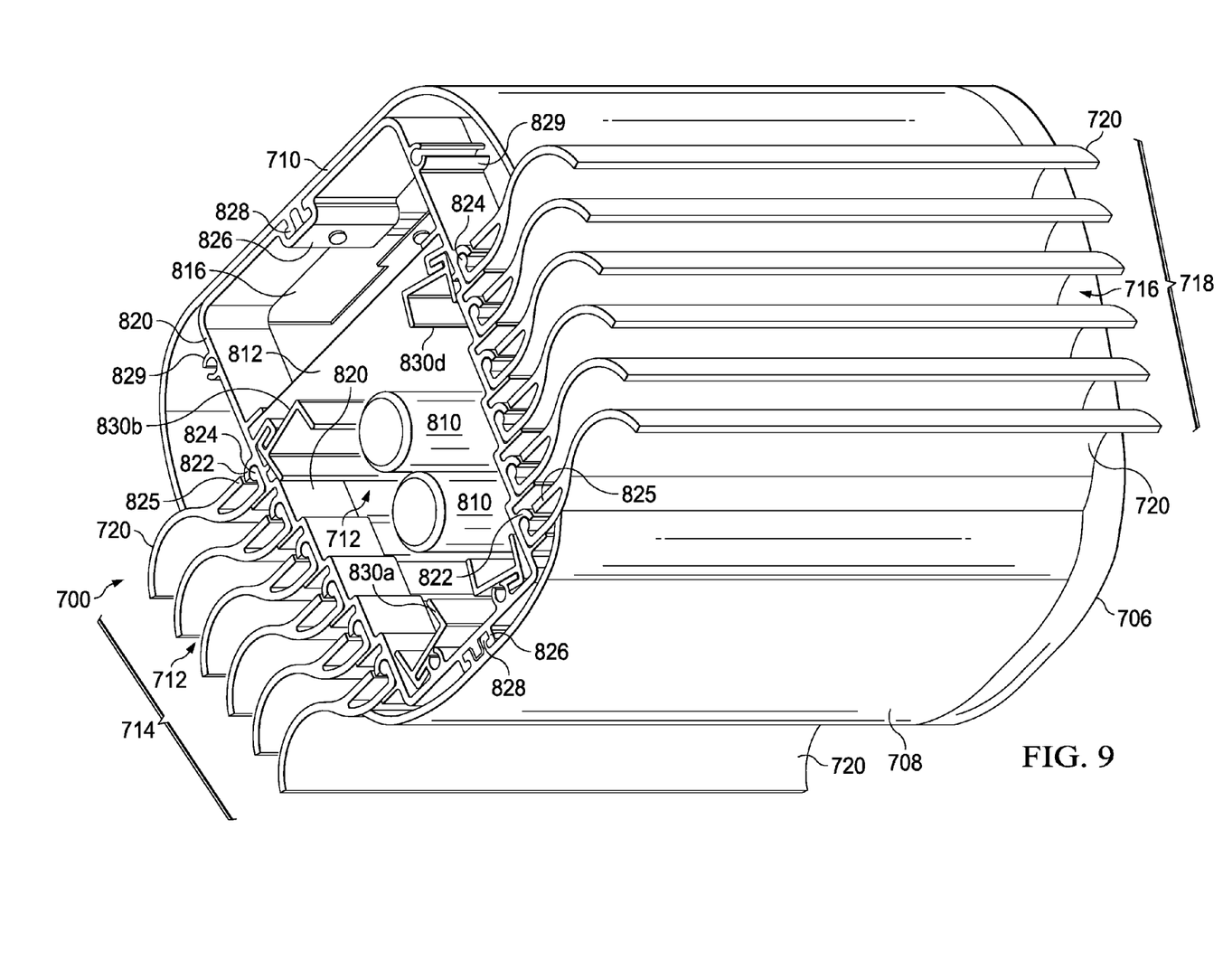
FIG. 9 is a fragmentary perspective view of the example embodiment of a photocatalytic device of FIGS. 7 and 8.

FIG. 7 is a perspective view of another example embodiment of a photocatalytic device (700) adapted for use with a mini-split system, such as shown in FIG. 1; FIG. 8 is a fragmentary, generally cross-sectional, end view of example photocatalytic device 700 of FIG. 7 (taken generally at one end cap); and FIG. 9 is a fragmentary perspective view of example photocatalytic device 700 of FIGS. 7 and 8. First with attention directed to FIG. 7, illustrated mini-split photocatalytic device 700 includes housing 702, adapted for deployment in conjunction with an air exchange intake 109 of an indoor unit 101 of a mini-split system 100. Housing 702, may, externally, include an end cap, 704 or 706, disposed on each end of photocatalytic device 700. Front valance 708 may be disposed across a front of photocatalytic device 700, extending between end caps 704 and 706. Correspondingly, back panel 710 may be disposed across a back of the photocatalytic device, also extending between end caps 704 and 706. Photocatalytic device inlet 712 may be defined by end caps 704 and 706, front valance 708, and back panel 710, on a first side, or nominal top, of photocatalytic device 700, with baffle 714 (made up of fins 720, discussed in greater detail below) extending therefrom. Correspondingly, photocatalytic device outlet 716 may also be defined by end caps 704 and 706, front valance 708, and back panel 710, on a second side (opposite the first), or nominal bottom, of photocatalytic device 700, with baffle 718 (also made up of fins 720, discussed below) extending therefrom.

Turning now to FIGS. 8 and 9, first absorbefacient filter 802 is shown positioned at inlet area 712 of housing 702, and first catalyst substrate 804 is shown positioned at the inlet area of the housing, as well, but disposed at the inner side on of the first absorbefacient filter. Second catalyst substrate 806 is shown positioned at outlet area 716 of housing 702, with second absorbefacient filter 808 positioned at outlet area 716, but, disposed at an outer side of the second catalyst substrate. Ultraviolet light from source 810 illuminates photocatalytic substrates 804 and 806. Ultraviolet light source 810 is located within housing 702 and shown positioned between first and second catalyst substrates 804 and 806. Hence, ultraviolet light source 810 is also positioned near photocatalytic substrates 804 and 806. First and second catalyst substrates 804 and 806 are preferably adapted to support a hydroxyl radical reaction with ultraviolet light from ultraviolet light source 810 and atmospheric water vapor that results in hydro peroxides and hydroxyl ions. In various embodiments, the photocatalytic structures 804 and 806 may also be comprised of a plurality of fluted structures arranged in a honeycomb formation. Reflector or plate 812 is shown spanning a back of housing 702. Reflector plate 812 may be adapted to reflect light from the ultraviolet light source toward first and second catalyst substrates 804 and 806 and/or may be coated with a photocatalytic coating, such as the manganese dioxide and/or Titanium dioxide coating(s) discussed below. Additionally, ultraviolet light source 810 may include further components such as bulb base 814 and ballast 816.

Ultraviolet light source 810 may also be a high-intensity, broad-spectrum ultraviolet bulb or tube. In other embodiments, the ultraviolet source may be a low-pressure fluorescent quartz bulb or a medium pressure amalgam lamp. Ultraviolet light falls in the band of light between 185 nm and 400 nm. There are three distinct bands of light within the ultraviolet spectrum: UV-A, UV-B, and UV-C. Longwave UV light (315 nm to 400 nm), or UV-A, refers to what is commonly called "black light." Midrange UV (280 nm to 315 nm), or UV-B, causes sunburn. Germicidal UV light (185 nm to 280 nm), or UV-C, is effective in microbial control. Research has demonstrated that the most efficient frequency for microbial destruction is between 254 nm and 265 nm within the UV-C band. Germicidal lamps that produce the majority of their output in this range have proven to be effective in microbial control/destruction.

Photocatalytic substrates 804 and 806 may also be a hydrated catalytic matrix, such as a hydrated quad-metallic catalyst. When ultraviolet light impacts photocatalytic structures 804 and 806, ozone is produced in the catalytic matrix. The catalyst supports a hydroxyl radical reaction with water vapor that results in hydro peroxides, hydroxyl ions, super oxide ions, passive negative ions hydroxides, and ozonide ions. These are highly reactive chemical species. The hydroxyl radicals are very strong oxidizers and will attack organic materials. This creates oxidation that helps to reduce odors, volatile organic compounds (VOCs), airborne viruses, bacteria, mold and other types of air pollution. The quad-metallic catalytic matrix may be comprised of Manganese dioxide, Titanium dioxide, Titanium, Zinc, Platinum, Gold, Silver, Copper, Rhodium, Ruthenium, Lanthanum, and Fluoride, for example. In other embodiments, other combinations of rare and noble metals may be used in a multi-metallic catalytic matrix. Additional elements, such as Carbon may also be included in the catalytic matrix. Absorbefacient filters 802 and 808 may include or incorporate absorbents material such as Zeolite, Potassium Permanganate, (activated) Carbon, or the like. Additionally or alternatively. Additional or alternative embodiments of the catalytic substrates 804 and 806 may also comprise adsorbent materials, such as one or more of Zeolite, Potassium Permanganate, (activated) Carbon, or the like. In either case, adsorbents may be used to capture molecular-sized pollutants, odors, and non-particulates and to remove VOCs.

In particular embodiments, photocatalytic substrates 804 and 806 may comprise a honeycomb aluminum, polymer, or similar formation, which may be etched w/acid, and which may then be dipped in an activated carbon slurry or the like. Thereafter, a Manganese dioxide coating may be sprayed on the formation, which is then baked, before a Titanium dioxide coating is sprayed on the formation and baked again. Further treatment of the photocatalytic substrate may include deposition of Zinc, Rhodium, Platinum, or the like on the substrate.

As noted, a plurality of fins (720) forming baffle 714 are disposed across inlet opening 712 defined by housing 702, while another plurality of fins (720) are disposed across outlet opening 716 defined in housing 702, forming baffle 718. These fins (720) are generally identical, and individually shaped and positioned together so as to prevent light from ultraviolet light source 810 from exiting housing 702, and generally reflecting of deflecting light from the ultraviolet light source striking the fins back into the housing. As seen in FIGS. 7, 8 and 9, these fins may each have a generally S-shaped cross section, so as to provide this reflective function, and to nest with one another to facilitate closing at least a portion of the inlet and/or outlet as described below.

To these ends, a plurality of frames 820 defining corresponding, fin receptive channels 822, may be disposed in housing 702. Each channel 822 may be configured to receive a base bead 824 of a fin (720) and rotatably support the fin from generally perpendicular to the opening (712 or 716) the fin is disposed across, to a generally deployment, closing at least a portion of the opening the fin is disposed across. As noted, in such a generally horizontal disposition the fins may nest with one another, effectively sealing at least a portion of the inlet or outlet. Fins 720 may also include stops 825 extending to abut an outer surface of the fin's corresponding channel 822 to stop rotation of the fin about channel 822 generally perpendicular to the respective inlet or outlet opening.

Frames 820 may each be adapted to be secured to front valance 708 and/or back panel 710, which may provide rigidity to housing 702. Embodiments may employ two frames 820, one disposed at each end of photocatalytic device housing 702. However, an intermediate frame could similarly support (longer) fins 720 and further secure front valance 708 and/or back panel 710, which may facilitate providing desired rigidity to a longer photocatalytic device housing. Thereby, embodiments of present photocatalytic device 700 may be (horizontally) "scalable," facilitating manufacture of photocatalytic devices of various lengths for use with mini-split system indoor units of with intake exchanges of various widths. Additionally, each of frames 820 may be adapted for end cap 704 or 706 to be secured thereto. The end caps, front valance and/or back panel may be secured to frames 820 through the use of screws, rivets or other fasteners. As shown in FIGS. 8 and 9 such fasteners may be pass through structure 826 in frame 820 into structures 828 defined by an interior surface, such as an interior of front valance 708 and/or back panel 710. Conversely, in other instances fasteners may pass through housing elements to be secured to frames 820, such as through end caps 704 and 706, to be secured into structures 829 in frames 820 to secure end caps 704 and 706 onto the rest of housing 702. While some elements may be secured to frames using more permanent means such as the aforementioned rivets, at least one end cap (such as end cap 704 in the illustrated embodiment) may be secured using screws, so that this end cap may be removed and replaced for servicing of catalyst substrates 804 and/or 806 and/or absorbefacient filters 802 and/or 808.

Illustrated housing 702 further comprises a pair of correspondingly positioned catalyst substrate and/or absorbefacient filter retention rails 830 (i.e. 830*a* and 830*b* or 830*c* and 830*d*). Rails 830 may be generally identical and may be sized and spaced to retain each of catalyst substrates 804 and/or 806 and/or absorbefacient filters 802 and/or 808 across the housing adjacent inlet 712 or outlet. In particular, in the illustrated embodiment, a first pair of corresponding catalyst substrate and absorbefacient filter retention rails 830*a* and 830*b* are spaced to retain catalyst substrate 804 and absorbefacient filter 802 across housing inlet 712, on a first side of ultraviolet light source 810. That is, as illustrated, absorbefacient filter 802 may preferably be retained by first pair of rails 830*a* and 830*b* in a position (immediately) adjacent the inlet, and catalyst substrate 804 may preferably be retained by first pair of rails 830*a* and 830*b* in a position (immediately) adjacent ultraviolet light source 810, on the aforementioned first side of the ultraviolet light source. Correspondingly, as also illustrated, second pair of corresponding catalyst substrate and absorbefacient filter retention rails 830*c* and 830*b* may also be spaced to retain one of the catalyst substrates (such as catalyst substrate 806) and one of the absorbefacient filters (such as filter 808) across housing outlet 716, on a second side of ultraviolet light source 810, opposite the first side thereof. In the particular illustrated embodiment absorbefacient filter 808 is shown retained by second pair of rails 830*c* and 830*d* in a positioned (immediately) adjacent outlet 716 and catalyst substrate 806 is retained by second pair of rails 830c and 830d in a position (immediately) adjacent ultraviolet light source 810, on the second side of the ultraviolet light source, relative to the first. Further, first and second pairs of rails 830a and b and 830c and d may retain each of first and second substrates 804 and 806 (as well as the accompanying filters 802 and 808, as shown) at an acute angle relative to reflector 812, such that UV light reflected from Ultraviolet light source 810 by reflector 812 may strike first and second substrates 804 and 806. Frames 820 and rails 830 may be formed from extruded material such as extruded aluminum (for rigidity) or a resilient material such as a polymer plastic, or the like.

Titanium dioxide may be used for water and air treatment as well as for catalytic production of gases. For example, Titanium dioxide may be used as a photocatalyst for the remediation of contaminated water because it is highly active under UV irradiation, stable, non-toxic, and inexpensive. The properties of Titanium dioxide, such as surface area, surface charge, crystallinity, surface crystalline plane, particle size, density of surface functional groups, and lattice defects, influence the photocatalytic activities in a complex way. The surface property of Titanium dioxide is particularly important in determining the photocatalytic reaction kinetics, mechanisms, and efficiencies because the photocatalytic reactions mostly take place on the surface. The surface modification of Titanium dioxide include polymer coating, metal deposition, anion complexation, and hybridization with silica. Such modifications of the Titanium dioxide surface enhance the photocatalytic efficiencies, change the reaction mechanisms, or alter the distribution of intermediates and products.

Each surface modification method has its unique role in affecting the kinetics and mechanisms of photocatalytic reactions. The Platinization of Titanium dioxide (e.g., Pt/TiO2) exhibits enhanced activities for many photocatalytic reactions. It is believed that Platinum deposits on Titanium dioxide attract and hold electrons with retarding their recombination with holes. Moreover, Titanium dioxide modified with both Fluoride and Platinum (e.g., F—TiO2/Pt) exhibits a unique photocatalytic activity for the anoxic degradation of phenolic compounds and the H2 production accompanied by the degradation of phenolic compounds.

Manganese dioxide exhibits thermocatalytic activity for the decomposition of organic pollutants. Coupling Titanium dioxide with Manganese dioxide degrades organics further than Titanium dioxide alone, due to the thermocatalytic activity of Manganese dioxide and enhanced UV-light irradiation photocatalytic activity of the Titanium dioxide. Hence, in accordance with embodiments of the present systems and methods Manganese dioxide, such as in combination with Titanium dioxide may be used not only in photocatalytic structures and substrates 203, 204, 503, 602, 804 and 806, but may also be used to coat interior surfaces of photocatalytic devices 200 and 700, such as, not only reflectors 205, 206 and 812, but also other interior surfaces of housings 201 and 702, such as, by way of example, the interior of end caps 704 and 706, the interior surface of front valance 708, and/or the interior surface of back panel 710. Such interior coatings provide a further advantage in that they can protect these housing components from the UV light emitted by UV light source 810. This enables production of housing components such as end caps 704 and 706, front valance 708, and/or back panel 710 from plastic (which may normal degrade in the presence of such intense UV light). Additionally, fins 718 may be coated with a Manganese dioxide and Titanium dioxide coating, particularly since the UV light being blocked and/or reflected back into the housing may enhance catalytic reaction on the surfaces of the fins as air passes over them. Moreover, other surfaces present within housing 702 may be coated with a Manganese dioxide and Titanium dioxide coating, such as surfaces of frames 820 and rails 830.

In some embodiments, the photocatalytic destruction of organics begins with its excitation by supra-band-gap photons, and continues through redox reactions where OH radicals, formed on the photocatalyst surface, play a major role. The presence of Gold and Platinum in the vicinity of Titanium dioxide may improve the performance of the photocatalyst. This effect has been attributed to a better charge separation between the photo-induced charge carriers and to an ability of the metal to prevent the deactivation of the photocatalyst, probably by a spillover mechanism that supplies oxygen to the Titanium dioxide surface. In addition to Platinum, other metallic elements may be used as catalysts either alone or in combination with other elements. For example, Ruthenium and Lanthanum may also be used as catalysts alone or in combination with other metals.

Embodiments of photocatalytic device 700 are passive, in that they do not include a forced air fan or the like. As noted, photocatalytic device 700 is adapted to be deployed in conjunction with an air exchange register of the indoor unit of a mini-split HVAC system. Photocatalytic device 700 may be placed on a typically horizontal return register of the indoor unit with fins of (lower) outlet baffle 718 generally indexing with slats of the return register. Air is pulled into (upper) inlet baffle 714, and through photocatalytic device 700 by the indoor unit. The air flowing through photocatalytic device 700 is purified in the manner described above, through photocatalytic action, and passes into the mini-split indoor unit through outlet baffle 718.

At least one ionizer, or ion generator, (not shown) may also be disposed in housing 201 or 702 to provide ions within the housing so that air circulated through the housing carries the ions out of the housing and/or so that oppositely charged ions are neutralized. Such an ionizer may be of the "needle-type," wherein a high voltage is applied to a needle to produce ions, and/or the ionizer(s) may be of a carbon fiber-based type" where the high voltage is applied to a carbon fiber mat or set of filaments or bristles to produce ions. The ionizer(s) may thus generate negative and/or positive ions using the relatively high voltage to ionize air molecules, such as through needlepoint ionization, or the like. Thus, the aforementioned hydro peroxides and hydroxyl ions are circulated into the indoor unit of the mini split system, by air flowing through housing.

Various photocatalytic device embodiments may include wireless means for controlling and monitoring various aspects of the photocatalytic device. For example, a sensor (not shown) may be coupled to the photocatalytic device. This sensor may be configured to determine a status of the photocatalytic device, and a transmitter coupled to the sensor may be configured to transmit an indication of the status to a controller, a personal computer, and/or portable computing device, such as a smartphone, tablet computing device, media player, or the like. In some cases, the controller may include a Heating, Ventilation, and/or Air Conditioning (HVAC) thermostat to display the status to a user. In such embodiments, the controller may be a network router or modem. Further, in such embodiments, the personal computer, and/or portable computing device may function as a controller, in that a user may control operation of the photocatalytic device, such as in response to display of the status, through wireless commands from the personal computer, and/or portable computing device to a (wireless) receiver in the photocatalytic device.

In some such implementations, the photocatalytic device may include a temperature sensor coupled to the media air filter (e.g. 802 and/or 808) and/or catalyst substrate(s) (e.g. 203, 204, 804, and/or 806), or the like. The status may include an indication of a level of airflow obstruction of the media air filter, the level of airflow obstruction determined based upon a temperature captured by the temperature sensor. In other implementations, the photocatalytic device sensor(s) may include a voltage or current detector coupled to a ballast (816) configured to power the UV light source (202 or 810). Also, the status may include an indication of an expected remaining lifespan of the UV light source, the expected remaining lifespan of the UV light source determined based upon a voltage or current determined by the voltage or current detector. The transmitted status may additionally or alternatively include at least one of: whether the photocatalytic device is present, whether the photocatalytic device is functioning properly, or an expected remaining lifespan of the photocatalytic device. The transmitter may include a wireless transmitter configured to implement a WiFi (IEEE 802.11), BLUETOOTH, ZIGBEE, ECOBEE, RED LINK, WEAVE, and/or (a) similar protocol(s). In some illustrative, non-limiting embodiments, a photocatalytic device may include one or more sensors configured to monitor a replaceable component in the photocatalytic device and to report a status of the replaceable component using a wireless communication protocol, such as described above. Such a replaceable component may include a media air filter, catalyst substrate, or a UV light source, such as also discussed above. In any such embodiments, the one or more sensors may include at least one of a: temperature sensor, a pressure sensor, an airflow sensor, a noise or sound sensor, a humidity sensor, an electromagnetic radiation sensor, a bioaresosol sensor, or a Volatile Organic Compounds (VOC) sensor, or the like. Also, in any such embodiments, the sensor(s) may report a power status of the photocatalytic device and/or components thereof, a UV lamp on/off condition, a UV light intensity, a wireless signal strength, pressure, humidity, temperature, and/or the like.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A ductless heating and air conditioning system photocatalytic device, comprising:
a housing adapted for deployment in conjunction with an air exchange intake of an indoor unit of a mini-split system, airflow passing through the housing into the air exchange intake of the indoor unit of the mini-split system, at least a portion of an interior surface of the housing coated with a Manganese dioxide and Titanium dioxide coating;
a first catalyst substrate positioned at an intake area of the housing;
a second catalyst substrate positioned at an exhaust area of the housing, the first and second catalyst substrates adapted to support a hydroxyl radical reaction with ultraviolet light and water vapor that results in hydro peroxides and hydroxyl ions;
an ultraviolet light source located within the housing and positioned between the first and second catalyst substrate; and
at least one Manganese dioxide and Titanium dioxide coated reflectors located within the housing and positioned adjacent to the first and second catalyst substrates to distribute reflected light from the ultraviolet light source across a surface of the catalyst substrates,
wherein the first catalyst substrate and the second catalyst substrate are positioned at an acute angle relative to each other and to the at least one reflector in a triangular arrangement with the ultraviolet light source in the middle of the first catalyst substrate, the second catalyst substrate, and the at least one reflector.

2. The photocatalytic device of claim 1, wherein the catalyst substrates comprise a hydrated multi-metallic catalyst, the catalyst comprising a plurality of compounds and/or elements selected from Manganese dioxide, Titanium dioxide, Titanium, Zinc, Platinum, Gold, Silver, Copper, Rhodium, Ruthenium, Lanthanum, and/or Fluoride.

3. The photocatalytic device of claim 1, further comprising at least one ionizer disposed in the housing, adapted to provide ions within the housing.

4. The photocatalytic device of claim 3, wherein the at least one ionizer is a needle type ionizer and/or a carbon fiber type ionizer, and wherein the at least one ionized produces either positively charged ions or negatively charged ions.

5. The photocatalytic device of claim 1, further comprising:
at least one sensor coupled to the photocatalytic device, the sensor configured to determine a status of the photocatalytic device; and
a wireless transmitter coupled to the sensor, the transmitter configured to transmit an indication of the status to a controller, a personal computer, and/or a portable computing device.

6. The photocatalytic device of claim 5, further comprising a wireless receiver adapted to receive commands from the controller, the same or a different personal computer, and/or the same or a different portable computing device to control operation of the ultraviolet light source.

7. A method of manufacturing a ductless heating and air conditioning system photocatalytic device, comprising:
providing an ultraviolet light source within a housing, the housing adapted for deployment in conjunction with an air exchange intake of an indoor unit of a mini-split system, airflow passing through the housing into the air exchange intake indoor unit of the mini-split system;
coating at least a portion of an interior of the housing with a Manganese dioxide and Titanium dioxide coating;
providing a first catalyst substrate and a second catalyst substrate within the housing, wherein the catalyst substrates are adapted to support a hydroxyl radical reaction with ultraviolet light and water vapor that results in hydro peroxides and hydroxyl ions;

providing at least one Manganese dioxide and Titanium dioxide coated reflector within the housing; and positioning the reflector adjacent to the first and second catalyst substrates and at an acute angle relative to the first and second catalyst substrates in a triangular arrangement with the ultraviolet light source in the middle of the first catalyst substrate, the second catalyst substrate, and the at least one reflector.

8. The method of claim 7, wherein the catalyst substrates comprise a hydrated multi-metallic catalyst, the catalyst comprising a plurality of compounds and/or elements selected from Manganese dioxide, Titanium dioxide, Titanium, Zinc, Platinum, Gold, Silver, Copper, Rhodium, Ruthenium, Lanthanum, and/or Fluoride.

9. The method of claim 7, further comprising disposing at least one ionizer in the housing, the at least one ionizer adapted to provide ions within the housing.

10. The method of claim 9, wherein the at least one ionizer is a needle type ionizer and/or a carbon fiber type ionizer, and wherein the at least one ionized produces either positively charged ions or negatively charged ions.

11. The method of claim 7, further comprising:
coupling at least one sensor to the photocatalytic device, the sensor configured to determine a status of the photocatalytic device; and
coupling a wireless transmitter to the sensor, the transmitter configured to transmit an indication of the status to a controller, a personal computer, and/or a portable computing device.

12. The method of claim 11 further comprising coupling a wireless receiver to the photocatalytic device to receive commands from the controller, the same or a different personal computer, and/or the same or a different portable computing device to control operation of the ultraviolet light source.

13. A ductless heating and air conditioning system photocatalytic device, comprising:
a housing adapted for deployment in conjunction with an air exchange intake of an indoor unit of a mini-split system, airflow passing through the housing into the air exchange intake of the indoor unit of the mini-split system;
a first absorbefacient filter positioned at an inlet area of the housing;
a first catalyst substrate positioned at the inlet area of the housing, disposed at an inner side the first absorbefacient filter;
a second catalyst substrate positioned at an outlet area of the housing;
a second absorbefacient filter positioned at the outlet area of the housing, disposed at an outer side of the second catalyst substrate;
an ultraviolet light source located within the housing and positioned between the first and second catalyst substrates, the first and second catalyst substrates adapted to support a hydroxyl radical reaction with ultraviolet light from the ultraviolet light source and water vapor that results in hydro peroxides and hydroxyl ions;
the housing further comprising a plurality of fins disposed across an inlet opening in the housing, the fins disposed across the inlet opening shaped to prevent light from the ultraviolet light source from exiting the housing and reflecting light from the ultraviolet light source striking the fins disposed across the inlet opening back into the housing;
the housing further comprising a plurality of fins disposed across an outlet opening in the housing, the fins disposed across the outlet opening shaped to reflect light from the ultraviolet light source striking the fins disposed across the outlet opening back into the housing; and a reflector spanning a back of the housing reflecting light from the ultraviolet light source toward the first and second catalyst substrates,
wherein the first catalyst substrate and the second catalyst substrate are positioned at an acute angle relative to each other and to the reflector in a triangular arrangement with the ultraviolet light source in the middle of the first catalyst substrate, the second catalyst substrate, and the reflector.

14. The photocatalytic device, of claim 13, wherein at least a portion of an interior of the housing is coated with a Manganese dioxide and Titanium dioxide coating.

15. The photocatalytic device, of claim 13, wherein the reflector is coated with a Manganese dioxide and Titanium dioxide coating.

16. The photocatalytic device of claim 13, wherein the catalyst substrates each comprise a hydrated multi-metallic catalyst, the catalyst comprising a plurality of compounds and/or elements selected from Manganese dioxide, Titanium dioxide, Titanium, Zinc, Platinum, Gold, Silver, Copper, Rhodium, Ruthenium, Lanthanum, and/or Fluoride.

17. The photocatalytic device, of claim 13, wherein the housing further comprises a plurality of frames defining corresponding, fin receptive channels, each channel configured to receive a base bead of a fin and support the fin generally perpendicular to the opening the fin is disposed across.

18. The photocatalytic device of claim 13, wherein the housing comprises:
an end cap disposed on each end of the housing/photocatalytic device;
a front valance disposed across a front of the photocatalytic device, extending between the end caps;
a back panel disposed across a back of the photocatalytic device, extending between the end caps.

19. The photocatalytic device of claim 13, wherein the housing further comprises:
a first pair of corresponding catalyst substrate and absorbefacient filter retention rails spaced to retain one of the catalyst substrates and one of the absorbefacient filters across the housing adjacent the inlet, on a first side of the ultraviolet light source; and
a second pair of corresponding catalyst substrate and absorbefacient filter retention rails spaced to retain one of the catalyst substrates and one of the absorbefacient filters across the housing adjacent the outlet, on a second side of the ultraviolet light source, opposite the first.

20. The photocatalytic device of claim 19, wherein the absorbefacient filter retained by the first pair of rails is positioned adjacent the inlet and the catalyst substrate retained by the first pair of rails is positioned adjacent the ultraviolet light source, on the first side of the ultraviolet light source, and the absorbefacient filter retained by the second pair of rails is positioned adjacent the outlet and the catalyst substrate retained by the second pair of rails is positioned adjacent the ultraviolet light source, on the second side of the ultraviolet light source.

21. The photocatalytic device of claim 20, wherein the first and second pair of rails retain each of the first and second substrates at an acute angle relative to the reflector.

22. The photocatalytic device of claim 13, further comprising at least one ionizer disposed in the housing, adapted to provide ions within the housing.

23. The photocatalytic device of claim 22, wherein the at least one ionizer is a needle type ionizer and/or a carbon fiber type ionizer, and wherein the at least one ionized produces either positively charged ions or negatively charged ions.

24. The photocatalytic device of claim 13, further comprising:
 at least one sensor coupled to the photocatalytic device, the sensor configured to determine a status of the photocatalytic device; and
 a wireless transmitter coupled to the sensor, the transmitter configured to transmit an indication of the status to a controller, a personal computer, and/or a portable computing device.

25. The photocatalytic device of claim 24, further comprising a wireless receiver adapted to receive commands from the controller, the same or a different personal computer, and/or the same or a different portable computing device to control operation of the ultraviolet light source.

\* \* \* \* \*